United States Patent
Lin

(10) Patent No.: US 9,164,043 B2
(45) Date of Patent: Oct. 20, 2015

(54) DETECTING METHOD AND DETECTING DEVICE

(71) Applicant: SHENZHEN CHINA STAR OPTOELECTRONICS TECHNOLOGY CO., LTD., Shenzhen, Guangdong (CN)

(72) Inventor: Yungyu Lin, Guangdong (CN)

(73) Assignee: SHENZHEN CHINA STAR OPTOELECTRONICS TECHNOLOGY CO., LTD., Shenzhen (CN)

(*) Notice: Subject to any disclaimer, the term of this patent is extended or adjusted under 35 U.S.C. 154(b) by 403 days.

(21) Appl. No.: 13/811,391

(22) PCT Filed: Dec. 13, 2012

(86) PCT No.: PCT/CN2012/086535
§ 371 (c)(1),
(2) Date: Jan. 22, 2013

(87) PCT Pub. No.: WO2014/089801
PCT Pub. Date: Jun. 19, 2014

(65) Prior Publication Data
US 2014/0160277 A1    Jun. 12, 2014

(51) Int. Cl.
*G01N 21/88* (2006.01)
*G01N 21/95* (2006.01)

(52) U.S. Cl.
CPC .... *G01N 21/8806* (2013.01); *G01N 2021/9513* (2013.01)

(58) Field of Classification Search
CPC  G01N 21/8806; G01N 21/95; G01N 21/9501
See application file for complete search history.

(56) References Cited

U.S. PATENT DOCUMENTS 6,476,388 B1 * 11/2002 Nakagaki et al. .......... 850/9
2002/0168787 A1 * 11/2002 Noguchi et al. ......... 438/16

(Continued)

FOREIGN PATENT DOCUMENTS

| CN | 1473360 A | 2/2004 |
|---|---|---|
| CN | 1735866 A | 2/2006 |
| CN | 1839308 A | 9/2006 |
| CN | 102798634 A | 11/2012 |
| KR | 20110070062 A | 6/2011 |
| KR | 20120006860 A | 1/2012 |

OTHER PUBLICATIONS

International Search Report of PCT Application No. PCT/CN2012/086535.

(Continued)

*Primary Examiner* — Jefferey Harold
*Assistant Examiner* — Sean Haiem

(57) ABSTRACT

The detecting method and detecting device provided in the present disclosure is used for detecting an array substrate, including: scanning a defect on the array substrate and determining a size of the defect; generating a switching controlling command according to the size of the defect and switching a lens to a magnification adapted to the size of the defect; and capturing an image of the defect using the switched lens. In the embodiment, by analyzing the size of the scanned defect and switching the camera lens according to the size of the defect, the switched lens is allowed to capture a complete and clear image of the defect, which eases the analysis of the type of the defect, effectively improves the analyzing accuracy of the defect, and improves the monitoring effect of the manufacturing process.

6 Claims, 6 Drawing Sheets

(56) References Cited

U.S. PATENT DOCUMENTS

2004/0207836 A1* 10/2004 Chhibber et al. .......... 356/237.4
2005/0254045 A1* 11/2005 Weiss et al. ................ 356/237.5
2011/0304848 A1* 12/2011 Tanaka et al. .............. 356/237.2
2013/0148116 A1*  6/2013 Tanaka ....................... 356/237.5

OTHER PUBLICATIONS

1st Office Action of counterpart Chinese Patent Application No. 201210528167.6 issued on May 6, 2014.

* cited by examiner

DETECTING METHOD AND DETECTING DEVICE

BACKGROUND

1. Technical Field

The present disclosure relates to detecting technologies, and particularly, to a detecting method and a detecting device applied to an array substrate of a liquid crystal panel.

2. Description of Related Art

The array substrate is one of the important components of a liquid crystal panel. In the manufacturing process of the array substrate, an AOI (Automatic Optic Inspection) system is used for detecting the array substrate. The AOI system detects the array substrate based on optical principles. The AOI system uses an optical scanning device to automatically scan the array substrate and collects images to detect a defect on the array substrate, and displays the defect on a display or labels the defect automatically such that the defect can be repaired by a maintainer. Generally, a usual detecting device includes a scanning lens having a single magnification. In the detection, the scanning lens is used for scanning and capturing an image of the array substrate. If the size of the defect is too large, the defect may go beyond the field of vision of the scanning lens and the image of the defect cannot be completely and clearly displayed; if the size of the detect is too small, the displayed image of the defect may be unclear and the type of the defect cannot be determined correctly.

SUMMARY

The present disclosure provides a detecting method and a detecting device which are capable of adjusting an imaging field of vision according to a size of a defect on an array substrate.

The detecting method provided in the present disclosure is used for detecting an array substrate, including: scanning a defect on the array substrate and determining a size of the defect; generating a switching controlling command according to the size of the defect and switching a lens to a magnification adapted to the size of the defect; and capturing an image of the defect using the switched lens.

Preferably, the step of generating a switching controlling command according to the size of the defect and switching a lens to a magnification adapted to the size of the defect includes: determining a predetermined size range in which the size of the defect is; generating the corresponding switching controlling command according to the predetermined size range; and switching the lens to the magnification corresponding to the predetermined size range.

Preferably, the step of switching the lens to the magnification corresponding to the predetermined size range includes: if the size of the defect is greater than or equal to 100 um, switching the lens to a five times magnification; if the size of the defect is greater than 20 um and less than 100 um, switching the lens to a ten times magnification; and if the size of the defect is less than or equal to 20 um, switching the lens to a fifty time magnification.

Preferably, the step of switching a lens to a magnification adapted to the size of the defect includes: controlling the lens switcher to move according to the switching controlling command to drive the corresponding lens on the lens switcher which has the magnification adapted to the size of the defect to move to be located above the defect.

Preferably, the step of generating a switching controlling command according to the size of the defect and switching a lens to a magnification adapted to the size of the defect includes: determining the predetermined size range in which the size of the defect is; generating the corresponding switching controlling command according to the predetermined size range; and switching the lens to the magnification corresponding to the predetermined size range.

Preferably, the step of switching the lens to the magnification corresponding to the predetermined size range includes: if the size of the defect is greater than or equal to 100 um, switching the lens to a five times magnification; if the size of the defect is greater than 20 um and less than 100 um, switching the lens to a ten times magnification; and if the size of the defect is less than or equal to 20 um, switching the lens to a fifty time magnification.

Preferably, the step of switching a lens to a magnification adapted to the size of the defect includes: adjusting the magnification of the lens according to the switching controlling command to allow the magnification of the lens to be adapted to the size of the defect.

Preferably, the step of generating a switching controlling command according to the size of the defect and switching a lens to a magnification adapted to the size of the defect includes: determining the predetermined size range in which the size of the defect is; generating the switching controlling command according to the predetermined size range; and switching the lens to the magnification corresponding to the predetermined size range.

Preferably, the step of switching a lens to a magnification adapted to the size of the defect includes: if the size of the defect is greater than or equal to 100 um, switching the lens to a five times magnification; if the size of the defect is greater than 20 um and less than 100 um, switching the lens to a ten times magnification; and if the size of the defect is less than or equal to 20 um, switching the lens to a fifty time magnification.

The detecting device provided in the present disclosure is used for detecting an array substrate, including: a lens; an optical instrument for scanning a defect on the array substrate and determining a size of the defect; and a lens switcher for generating a switching controlling command according to the size of the defect, controlling the lens to switch to a magnification adapted to the size of the defect, and controlling the switched lens to capture an image of the defect.

Preferably, the lens switcher includes: a size range determining unit for determining a predetermined size range in which the size of the defect is; a switching controlling command generator for generating the corresponding switching controlling command according to the predetermined size range; and a magnification switching unit for switching the lens to a magnification corresponding to the predetermined size range.

Preferably, the magnification switching unit is further used for: switching the lens to a five times magnification if the size of the defect is greater than or equal to 100 um; switching the lens to a ten times magnification if the size of the defect is greater than 20 um and less than 100 um; and switching the lens to a fifty times magnification if the size of the defect is less than or equal to 20 um.

Preferably, the lens switcher moves according to the switching controlling command to drive the corresponding lens on the lens switcher having the magnification adapted to the size of the defect to move to be located above the defect.

Preferably, the lens switcher includes: a size range determining unit for determining a predetermined size range in which the size of the defect is; a switching controlling command generator for generating the corresponding switching controlling command according to the predetermined size range; and a magnification switching unit for switching the lens to a magnification corresponding to the predetermined size range.

Preferably, the magnification switching unit is further used for: switching the lens to a five times magnification if the size of the defect is greater than or equal to 100 um; switching the lens to a ten times magnification if the size of the defect is greater than 20 um and less than 100 um; and switching the lens to a fifty time magnification if the size of the defect is less than or equal to 20 um.

Preferably, the lens switcher is used for adjusting the magnification of the lens according to the switching controlling command to allow the magnification of the lens to be adapted to the size of the defect.

Preferably, the lens switcher includes: a size range determining unit for determining a predetermined size range in which the size of the defect is; a switching controlling generator for generating the corresponding switching controlling command according to the predetermined size range; and a magnification switching unit for switching the lens to the magnification corresponding to the predetermined size range.

Preferably, the magnification switching unit is further used for: switching the lens to a five times magnification if the size of the defect is greater than or equal to 100 um; switching the lens to a ten times magnification if the size of the defect is greater than 20 um and less than 100 um; and switching the lens to a fifty times magnification if the size of the defect is less than or equal to 20 um.

In the embodiment, by analyzing the size of the scanned defect and switching the camera lens according to the size of the defect, the switched lens is allowed to capture a complete and clear image of the defect, which eases the analysis of the type of the defect, effectively improves the analyzing accuracy of the defect, and improves the monitoring effect of the manufacturing process.

DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment is this disclosure are not necessarily to the same embodiment, and such references mean at least one.

Figure 1:
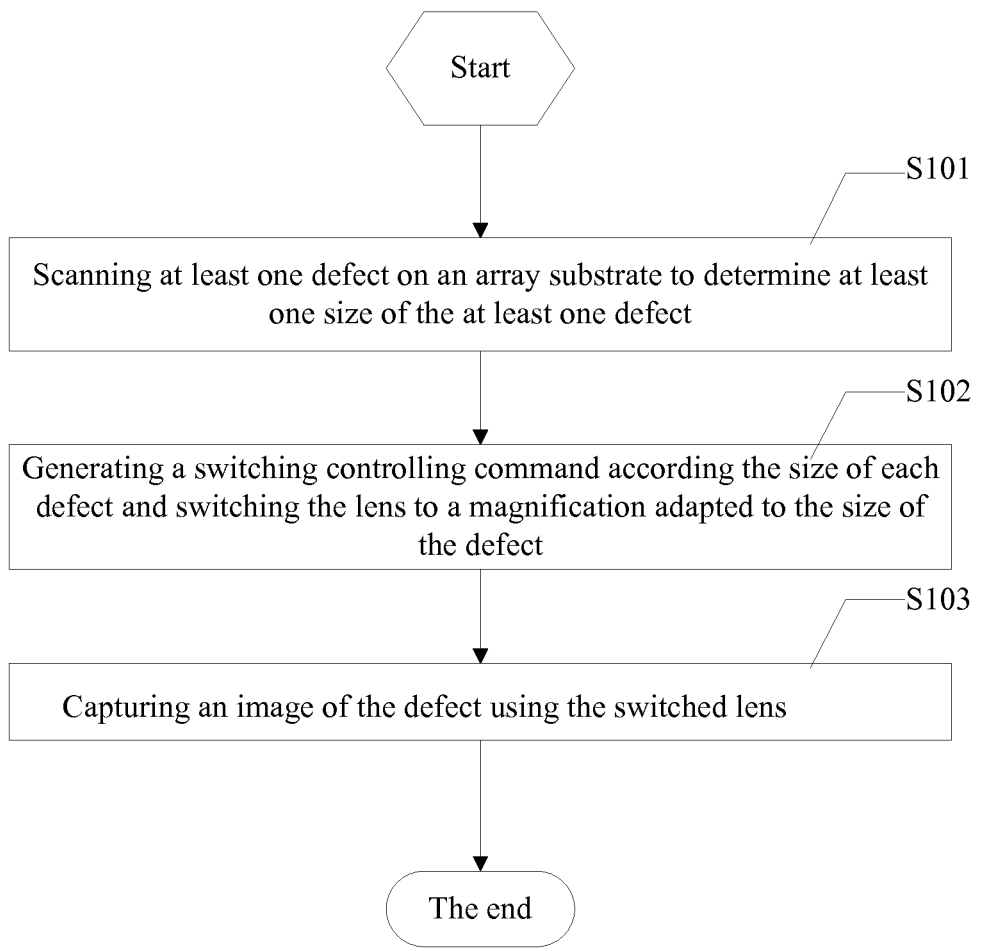
FIG. 1 is a flow chart of a detecting method in accordance with a first embodiment of the present disclosure.

Referring to FIG. 1, which is a flow chart of a detecting method in accordance with a first embodiment of the present disclosure. The detecting method of the present disclosure includes the following steps.

Step S101, scanning at least one defect on an array substrate to determine at least one size of the at least one defect.

In the embodiment, after the array substrate enters a detecting device, an optical scanning instrument of the detecting device scans the array substrate to determine the number of the defects on the array substrate and the sizes of the defects.

Step S102, generating a switching controlling command according to the size of each defect and switching the lens to a magnification adapted to the size of the defect.

To a respective defect, if the size of the defect is large, a magnification of a lens is decreased; if the size of the defect is small, the magnification of the lens is increased. The switching of the magnification of the lens can be realized by switching the lens. Different lenses have different magnifications. It is noted that the switching of the magnification can also be realized by using a lens having an adjustable magnification, thus, the magnification of the lens can be adjusted.

Step S103, capturing an image of the defect using the switched lens.

The switched lens has an appropriate field of vision corresponding to the size of the current defect and thus is capable of capturing an image of the current defect completely and clearly.

In the embodiment, by analyzing the size of the scanned defect and switching the camera lens according to the size of the defect, the switched lens is allowed to capture a complete and clear image of the defect, which eases the analysis of the type of the defect, effectively improves the analyzing accuracy of the defect, and improves the monitoring effect of the manufacturing process.

Figure 2:
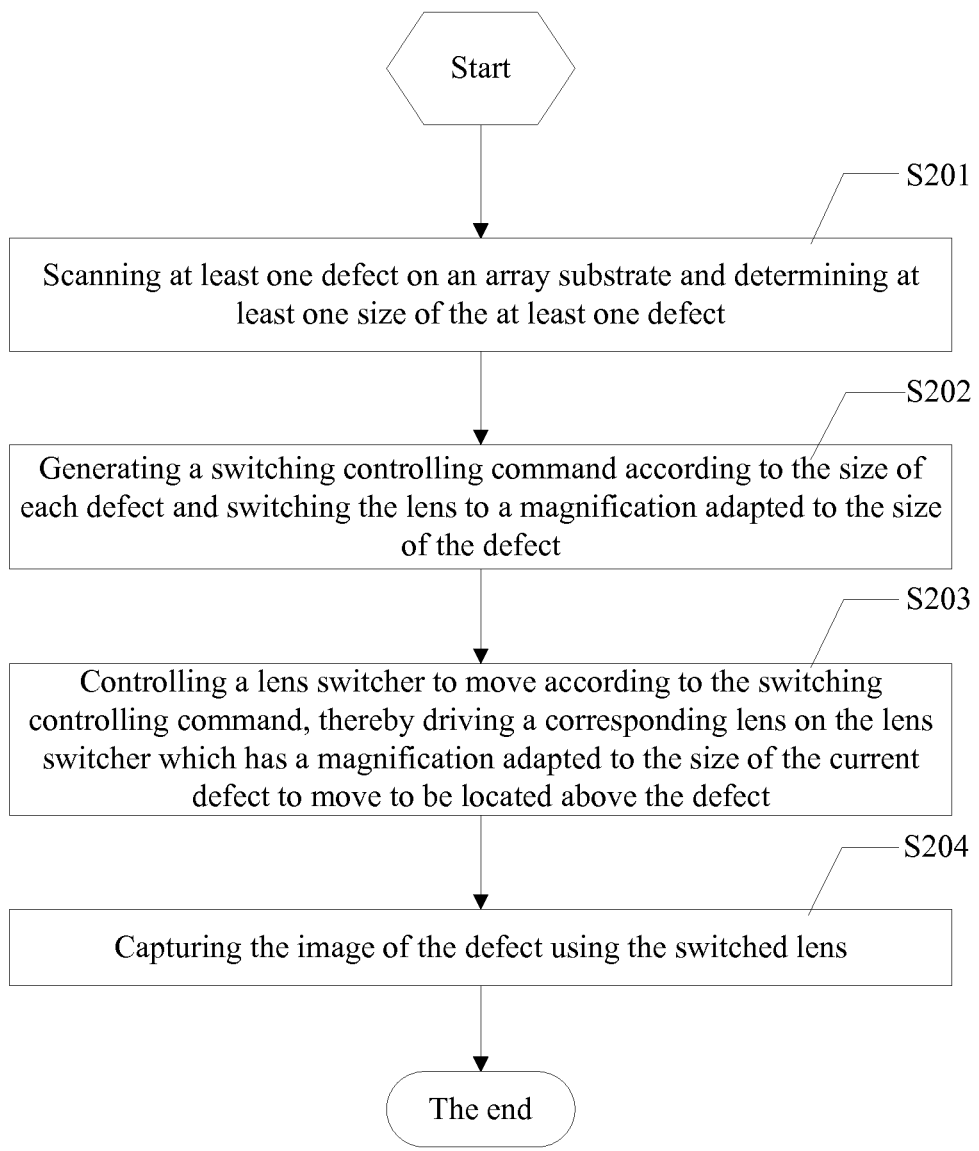
FIG. 2 is a flow chart of a detecting method in accordance with a second embodiment of the present disclosure.

Referring to FIG. 2, which is a flow chart of a detecting method in accordance with a second embodiment. The detecting method of the present disclosure includes the following steps.

Step S201, scanning at least one defect on an array substrate and determining at least one size of the at least one defect.

In the embodiment, after the array substrate enters a detecting device, an optical instrument of the detecting device scans the array substrate to determine the number of the defects on the array substrate and the sizes of the defects.

Step S202, generating a switching controlling command according to the size of each defect.

To a respective defect, if the size of the defect is large, the switching controlling command indicates a decrease in a magnification; if the size of the defect is small, the switching controlling command indicates an increase in the magnification.

Step S203, controlling a lens switcher to move according to the switching controlling command, thereby driving a corresponding lens on the lens switcher having a magnification adapted to the size of the current defect to move to be located above the defect.

The switching of the magnification of the embodiment is realized by switching lens. A number of lens having different magnifications, including lenses respectively having a twice magnification, a five times magnification, a ten times magnification, a twenty times magnification, and a fifty times magnification, are arranged on the lens switcher. The lenses may be arranged in a row or arranged in a circle. If the size of the defect is relatively large, the lens having a lower magnification can be used. By controlling the lens switcher to move, the lens having the five times magnification is driven to move to be located above the defect such that the lens having five times magnification can capture an image of the defect. If the size of the defect is relatively small, the lens having a higher magnification can be used. By controlling the lens switcher to move, the lens having the fifty times magnification is driven to move to be located above the defect such that the lens having the fifty times magnification can capture the image of the defect.

Step S204, capturing the image of the defect using the switched lens.

In the embodiment, by controlling the lens switcher to move according to the switching controlling command, the lenses can be driven to move to allow the lens adapted to the size of the current defect to be located above the defect, which realizes the switching of the magnification, eases the analysis of the type of the defect, and effectively improves the analyzing accuracy of the defect.

Figure 3:
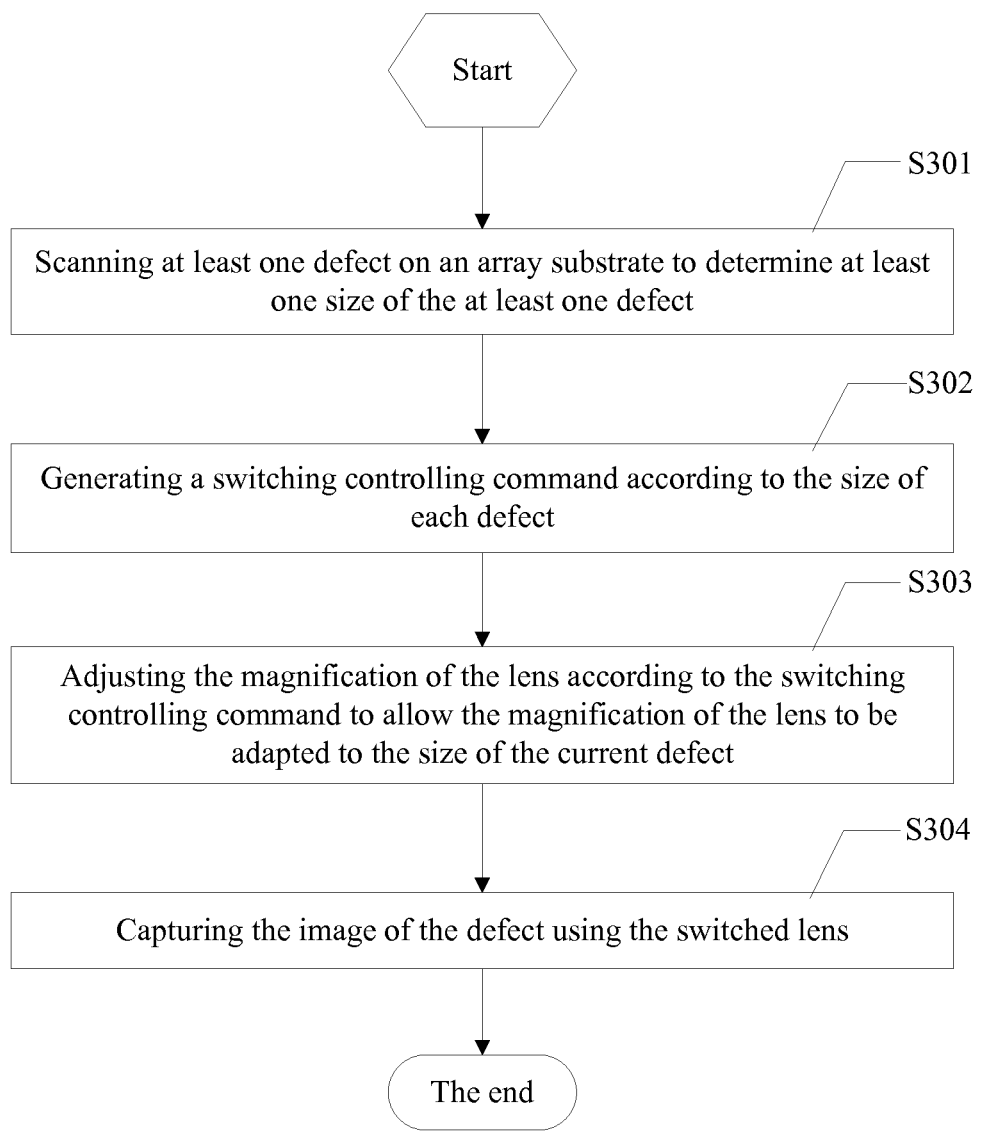
FIG. 3 is a flow chart of a detecting method in accordance with a third embodiment of the present disclosure.

Referring to FIG. 3, which is a flow chart of a detecting method in accordance with a third embodiment of the present disclosure. The detecting method of the embodiment includes the following steps.

Step S301, scanning at least one defect on an array substrate to determine at least one size of the at least one defect.

In the embodiment, after the array substrate enters a detecting device, an optical instrument of the detecting device scans the array substrate to determine the number of the defects on the array substrate and the sizes of the defects.

Step S302, generating a switching controlling command according to the size of each defect.

To a respective defect, if the size of the defect is large, the switching controlling command indicates a decrease in a magnification of a lens; if the size of the defect is small, the switching controlling command indicates an increase in the magnification of the lens.

Step S303, adjusting the magnification of the lens according to the switching controlling command to allow the magnification of the lens to be adapted to the size of the current defect.

In the embodiment, the lens having an adjustable magnification is connected to a lens switcher. If the size of the current defect is relatively large, the lens switcher decreases the magnification of the lens to allow the lens to capture an image of the defect at a lower magnification. If the size of the current defect is relatively small, the lens switcher increases the magnification of the lens to allow the lens to capture an image of the defect at a higher magnification.

Step S304, capturing the image of the defect using the switched lens.

In the embodiment, by adjusting the magnification of the lens according to the switching controlling command, the magnification of the lens is adapted to the size of the current defect, which realizes the switching of the magnification, eases the analysis of the type of the defect, effectively improves the analyzing accuracy of the defect, and improves the monitoring effect of the manufacturing process.

Figure 4:
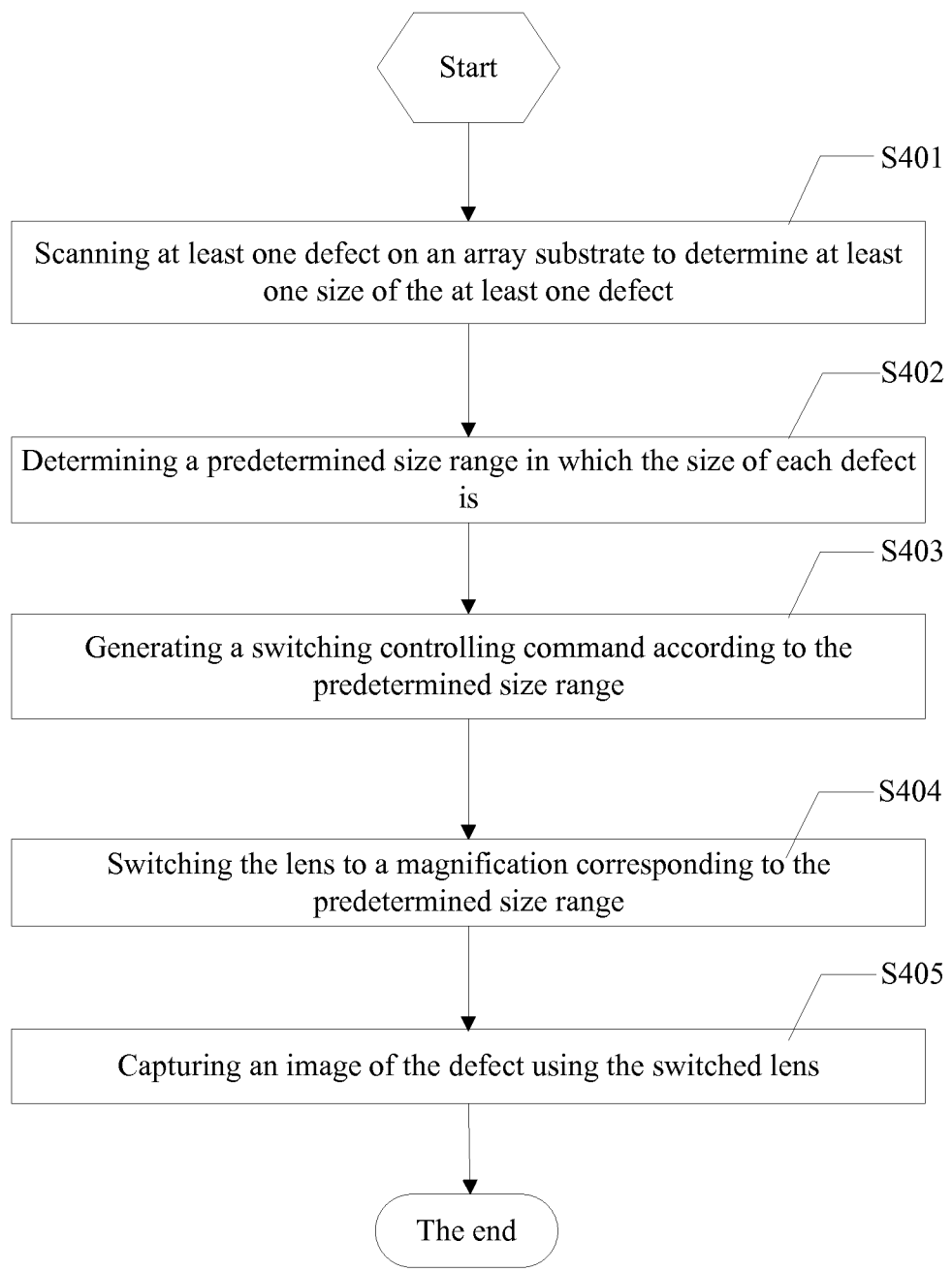
FIG. 4 is a flow chart of a detecting method in accordance with a fourth embodiment of the present disclosure.

Referring to FIG. 4, which is a flow chart of a detecting method in accordance with a fourth embodiment of the present disclosure. The detecting method of the embodiment includes the following steps.

Step S401, scanning at least one defect on an array substrate to determine at least one size of the at least one defect.

In the embodiment, after the array substrate enters a detecting device, an optical instrument of the detecting device scans the array substrate to determine the number of the defects on the array substrate and the sizes of the defects.

Step S402, determining a predetermined size range in which the size of each defect is.

A data table containing the size of each defect is used to obtain a mapped relationship between each predetermined size range and the corresponding magnification. Or, appropriate size ranges can be input manually to build the mapped relationship between each predetermined size range and the corresponding magnification. By judging which predetermined size range the size of the currently-scanned defect falls into, the size range of the current defect can be determined.

Step S403, generating a switching controlling command according to the predetermined size range.

After obtaining the predetermined size range, looking up a mapped relationship data table to obtain the magnification corresponding to the predetermined size range to generate the corresponding switching controlling command.

Step S404, switching the lens to a magnification corresponding to the predetermined size range.

According to the switching controlling command, the magnification of the lens is switched to correspond to the predetermined size range.

Step S405, capturing an image of the defect using the switched lens.

In the embodiment, by building the mapped relationship between each predetermined size range and the corresponding magnification, the required magnification can be obtained according to the size of the current defect, which allows the switched lens to capture a complete and clear image of the defect, eases the analysis of the type of the defect, and effectively improves the analyzing accuracy of the defect.

Figure 5:
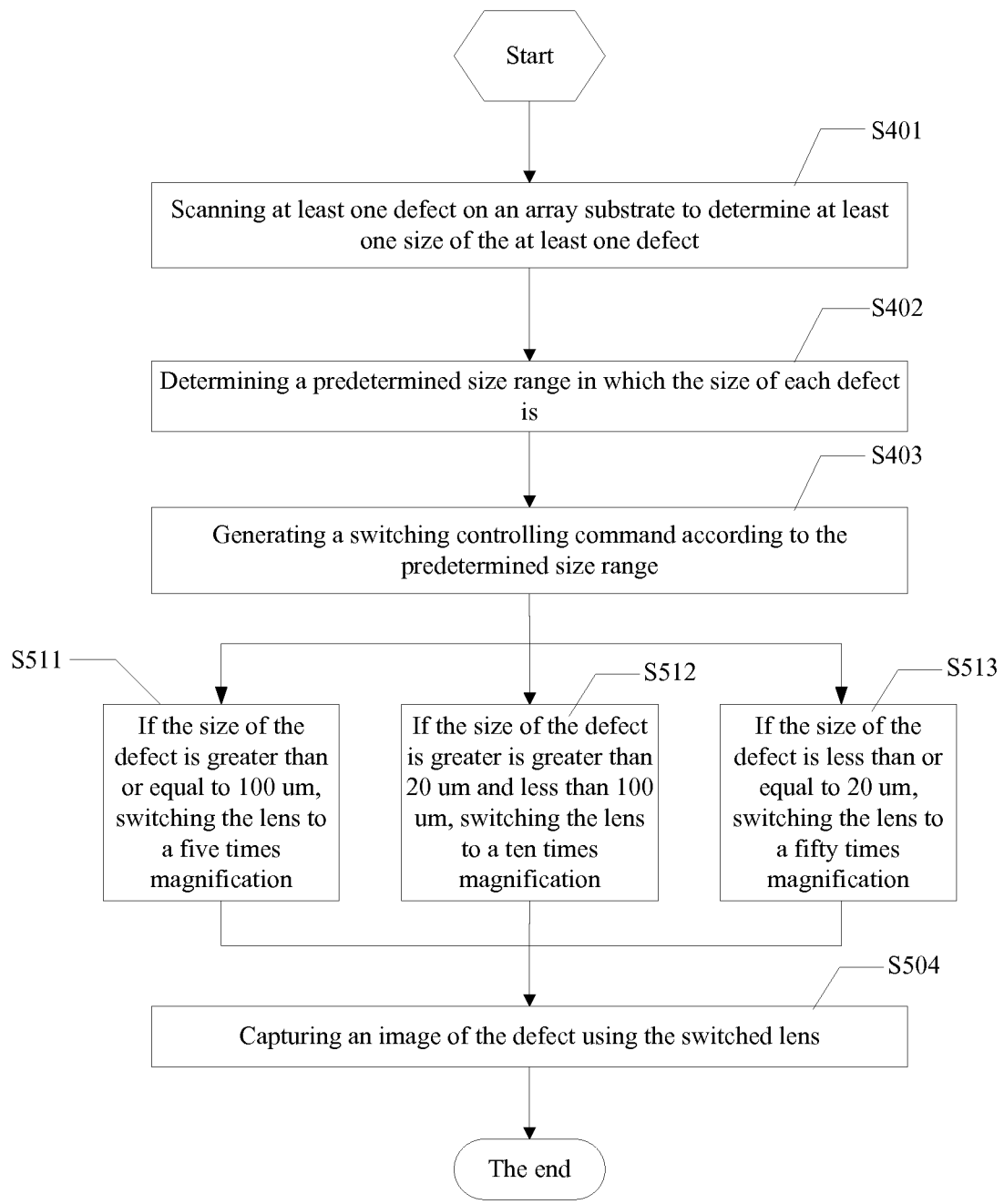
FIG. 5 is a flow chart of a detecting method in accordance with a fifth embodiment of the present disclosure.

Referring to FIG. 5, which is a flow chart of a detecting method in accordance with a fifth embodiment of the present disclosure. Based on the embodiment shown in FIG. 4, a step of determining the magnification is provided in the detecting method of the embodiment.

Step S501, scanning at least one defect on an array substrate to determine at least one size of the at least one defect.

In the embodiment, after the array substrate enters a detecting device, an optical instrument of the detecting device scans the array substrate to determine the number of the defects on the array substrate and the sizes of the defect.

Step S502, determining a predetermined size range in which the size of each defect is.

A data table containing the size of each defect is used to obtain a mapped relationship between each predetermined size range and the corresponding magnification. Or, appropriate size ranges can be input manually and the mapped relationship between each predetermined size range and the corresponding magnification can be built. By judging which predetermined size range the size of the currently-scanned defect falls into, the size range of the current defect can be determined.

Step S503, generating a switching controlling command according to the predetermined size range.

After obtaining the predetermined size range, looking up a mapped relationship data table to obtain the magnification corresponding to the predetermined size range to generate the corresponding switching controlling command. The step S503 includes:

step S511, if the size of the defect is greater than or equal to 100 um, switching the lens to a five times magnification;

step S512, if the size of the defect is greater is greater than 20 um and less than 100 um, switching the lens to a ten times magnification; and step S513, if the size of the defect is less than or equal to 20 um, switching the lens to a fifty times magnification.

Step S504, capturing an image of the defect using the switched lens.

Based on a five times magnification, a ten times magnification, and a fifty times magnification, the mapped relationships between the predetermined size ranges and the magnifications are shown in the following table:

| Predetermined size range | Magnification |
|---|---|
| ≥100 μm | Five times |
| 20 μm~100 μm | Ten times |
| ≤20 μm | Fifty times |

According to the mapped relationship between each predetermined size range and the corresponding magnification, the required magnification can be obtained, which allows the switched lens to capture a complete and clear image of the defect, eases the analysis of the type of the defect, and effectively improves the analyzing accuracy of the defect.

Figure 6:
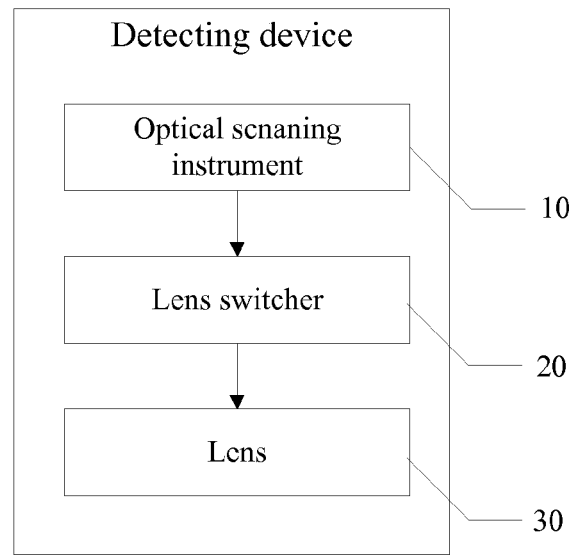
FIG. 6 is a schematic view of a detecting device in accordance with a first embodiment of the present disclosure.

Referring to FIG. 6, which is a detecting device in accordance with a first embodiment of the present disclosure. The detecting device of the present disclosure is used for detecting an array substrate, including an optical scanning instrument 10, a lens switcher 20, and at least one lens 30. The optical scanning instrument 10 is used for scanning at least one defect on the array substrate and determining at least one size of the at least one defect. The lens switcher 20 is used for generating a switching controlling command according to the size of each defect determined by the optical scanning instrument 10, controlling the at least one lens 30 to switch to a magnification adapted to the size of the defect according to the switching controlling command, and controlling the switched lens to capture an image of the defect.

In the embodiment, after the array substrate enters the detecting device, the optical scanning instrument 10 of the detecting device scans the array substrate to determine the number of the defects on the array substrate and the sizes of the defects. To a respective defect, if the size of the defect is large, the magnification of the lens 30 is increased; if the size of the defect is small, the magnification of the lens 30 is decreased. The switching of the magnification of the lens can be realized by switching the lens and different lens have different magnifications. Or, the switching of the magnification of the lens can be realized by using a lens having an adjustable magnification, thus, the magnification of the lens can be adjusted. The switched lens 30 has an appropriate field of vision corresponding to the current defect to capture a clear and complete image of the defect. In the embodiment, by analyzing the size of the scanned defect and switching the camera lens according to the size of the defect, the switched lens is allowed to capture a complete and clear image of the defect, which eases the analysis of the type of the defect, effectively improves the analyzing accuracy of the defect, and improves the monitoring effect of the manufacturing process.

The detecting device of the embodiment may include a number of lens 30 having different magnifications. The lens switcher 20 moves according to the switching controlling command to drive the corresponding lens 30 which has a magnification adapted to the size of the current defect to move to be located above the defect, thereby switching the lens 30. Specifically, the switching of the magnification of the embodiment is realized by switching the lens. A number of lens having different magnifications, including lenses having a twice magnification, a five times magnification, a ten times magnification, a twenty times magnification, and a fifty times magnification, are arranged on the lens switcher. The lenses may be arranged in a row or arranged in a circle. If the size of the defect is relatively large, the lens having a lower magnification can be used. By controlling the lens switcher to move, the lens having a five times magnification is driven to move to be located above the defect such that the lens having the five times magnification can capture the image of the defect. If the size of the defect is relatively small, the lens having a higher magnification can be used. By controlling the lens switcher to move, the lens having a fifty times magnification is driven to move to be located above the defect such that the lens having the fifty times magnification can capture the image of the defect.

The detecting device of the embodiment can include one lens 30 having an adjustable magnification. The lens switcher 20 adjusts the magnification of the lens 30 according to the switching controlling command to allow the magnification of the lens 30 to be adapted to the size of the current defect, thereby realizing the switching of the magnification of the lens 30. Specifically, the lens 30 having the adjustable magnification is connected to the lens switcher 20. If the size of the defect is relatively large, the lens switcher 20 decreases the magnification of the lens to allow the lens 30 to capture the image of the defect at a lower magnification. If the size of the defect is relatively small, the lens switcher 20 increases the magnification of the lens 30 to allow the lens 30 to capture the image of the defect at a higher magnification. In the embodiment, with the lens switcher 20 adjusting the magnification of the lens 30 according to the switching controlling command, the magnification of the lens 30 is allowed to be adapted to the current defect, which realizes the switching of the magnification, allows the lens 30 with the switched magnification to capture a clear and complete image of the defect, eases the analysis of the type of the defect, effectively improves the analyzing accuracy of the defect, and improves the monitoring effect of the manufacturing process.

Figure 7:
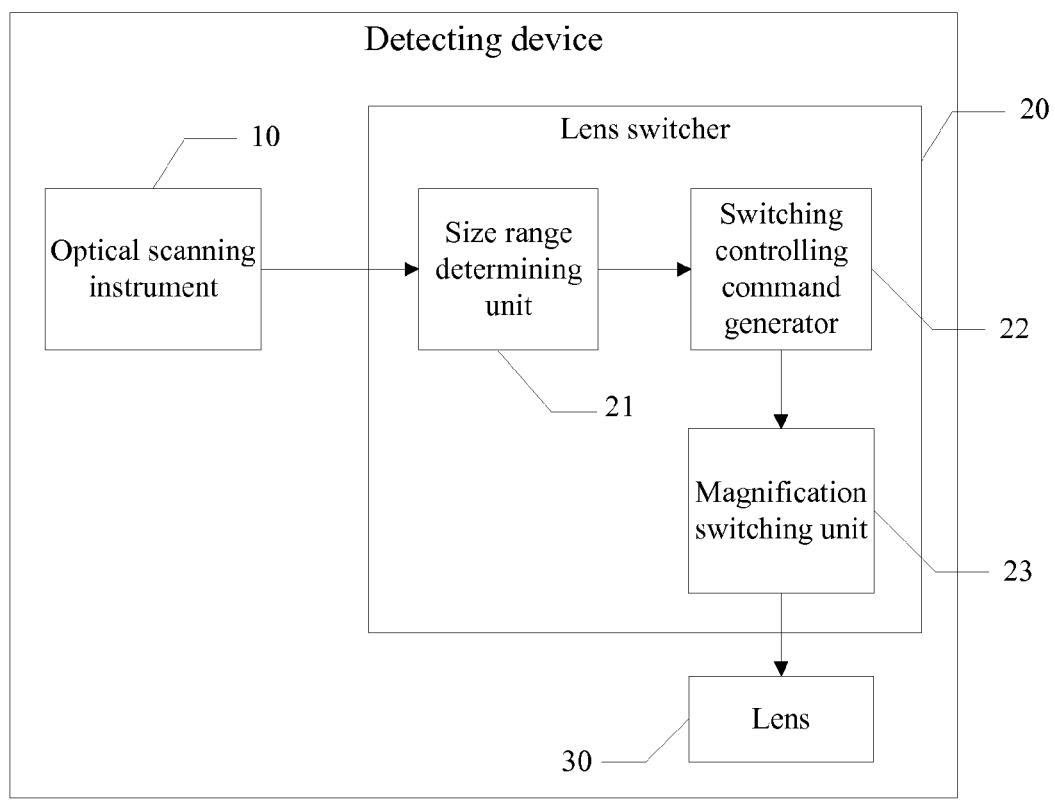
FIG. 7 is a schematic view of a detecting device in accordance with a second embodiment of the present disclosure.

Referring to FIG. 7, which is a detecting device in accordance with a second embodiment of the present disclosure. Based on the embodiment shown in FIG. 6, specific structure of the lens switcher 20 is described in the embodiment to explain the working process that the lens switcher 20 switches the lens 30 according to a size range of a defect. In the embodiment, the lens switcher 20 includes:

a size range determining unit 21 for determining a predetermined size range in which the size of each defect is;

a switching controlling command generator 22 for generating a corresponding switching controlling command according to the predetermined size range; and a magnification switching unit 23 for switching the lens 30 to a magnification corresponding to the predetermined size range.

A data table containing the size of each defect is stored in the detecting device of the embodiment for indicating a mapped relationship between each predetermined size range and the corresponding magnification. Or, appropriate size ranges can be input manually and the mapped relationship between each predetermined size range and the corresponding magnification can be built. The size range determining unit 21 is used for judging which predetermined size range the size of the defect falls into, the switching controlling command generator 22 looks up a mapped relationship data table to obtain a magnification corresponding to the corresponding predetermined size range after the size range determining unit 21 determines the size range, and generating the corresponding switching controlling command. The magnification switching unit 23 is used for switching the magnification of the lens 30 to a magnification corresponding to the predetermined size range according to the switching controlling command. In the embodiment, by building the mapped relationship between each predetermined size range and the corresponding magnification, the required magnification can be obtained according to the size of the current defect, thus, the switched lens 30 can capture a clear and complete image of the defect, which eases the analysis of the type of the defect and effectively improves the analyzing accuracy of the defect.

In the embodiment, the magnification switching unit 23 can switch the magnification according to the size range of the defect. The magnification switching unit 23 is further used for:

switching the lens to a five times magnification if the size of the defect is greater than or equal to 100 um;

switching the lens to a ten times magnification if the size of the defect is greater is greater than 20 um and less than 100 um; and switching the lens to a fifty times magnification if the size of the defect is less than or equal to 20 um.

Based on a five times magnification, a ten times magnification, and a fifty times magnifications, the mapped relationships between the predetermined size ranges and the corresponding magnifications are shown in the following table:

| Predetermined size range | Magnification |
| --- | --- |
| ≥100 μm | Five times |
| 20 μm~100 μm | Ten times |
| ≤20 μm | Fifty times |

Even though information and the advantages of the present embodiments have been set forth in the foregoing description, together with details of the mechanisms and functions of the present embodiments, the disclosure is illustrative only; and that changes may be made in detail, especially in matters of shape, size, and arrangement of parts within the principles of the present embodiments to the full extend indicated by the broad general meaning of the terms in which the appended claims are expressed.

What is claimed is:

1. A detecting method for detecting an array substrate, comprising:

scanning a defect on the array substrate and determining a size of the defect;

generating a switching controlling command according to the size of the defect and switching a lens to a magnification adapted to the size of the defect; and capturing an image of the defect using the switched lens;

wherein the step of generating a switching controlling command according to the size of the defect and switching a lens to a magnification adapted to the size of the defect comprises:

determining a predetermined size range in which the size of the defect is;

generating the corresponding switching controlling command according to the predetermined size range; and switching the lens to the magnification corresponding to the predetermined size range;

wherein the step of switching the lens to the magnification corresponding to the predetermined size range comprises:

when the size of the defect is greater than or equal to 100 um, switching the lens to a five times magnification;

when the size of the defect is greater than 20 um and less than 100 um, switching the lens to a ten times magnification; and when the size of the defect is less than or equal to 20 um, switching the lens to a fifty time magnification.

2. The detecting method as claimed in claim 1, wherein the step of switching a lens to a magnification adapted to the size of the defect comprises:

controlling the lens switcher to move according to the switching controlling command to drive the corresponding lens on the lens switcher which has the magnification adapted to the size of the defect to move to be located above the defect.

3. The detecting method as claimed in claim 1, wherein the step of switching a lens to a magnification adapted to the size of the defect comprises:

adjusting the magnification of the lens according to the switching controlling command to allow the magnification of the lens to be adapted to the size of the defect.

4. A detecting device for detecting an array substrate, comprising:

a lens;

an optical instrument for scanning a defect on the array substrate and determining a size of the defect; and a lens switcher for generating a switching controlling command according to the size of the defect, controlling the lens to switch to a magnification adapted to the size of the defect, and controlling the switched lens to capture an image of the defect;

wherein the lens switcher comprises:

a size range determining unit for determining a predetermined size range in which the size of the defect is;

a switching controlling command generator for generating the corresponding switching controlling command according to the predetermined size range; and a magnification switching unit for switching the lens to a magnification corresponding to the predetermined size range;

wherein the magnification switching unit is further used for:

switching the lens to a five times magnification when the size of the defect is greater than or equal to 100 um;

switching the lens to a ten times magnification when the size of the defect is greater than 20 um and less than 100 um; and switching the lens to a fifty times magnification when the size of the defect is less than or equal to 20 um.

5. The detecting device as claimed in claim 4, wherein the lens switcher moves according to the switching controlling command to drive the corresponding lens on the lens switcher having the magnification adapted to the size of the defect to move to be located above the defect.

6. The detecting device as claimed in claim 4, wherein the lens switcher is used for adjusting the magnification of the lens according to the switching controlling command to allow the magnification of the lens to be adapted to the size of the defect.

* * * * *